US009918880B2

(12) United States Patent
Swain et al.

(10) Patent No.: US 9,918,880 B2
(45) **Date of Patent: *Mar. 20, 2018**

(54) SYSTEMS FOR PROVIDING FLUID FLOW TO TISSUES

(71) Applicant: KCI Licensing, Inc., San Antonio, TX (US)

(72) Inventors: Larry D. Swain, San Antonio, TX (US); Michael E. Manwaring, San Antonio, TX (US); Douglas A. Cornet, Charlottesville, VA (US); Braden King-Fung Leung, San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 1010 days.

This patent is subject to a terminal disclaimer.

(21) Appl. No.: 14/252,644

(22) Filed: Apr. 14, 2014

(65) Prior Publication Data

US 2014/0276251 A1 Sep. 18, 2014

Related U.S. Application Data

(62) Division of application No. 12/648,448, filed on Dec. 29, 2009, now Pat. No. 8,734,409.

(Continued)

(51) Int. Cl.

*A61M 1/00* (2006.01)
*A61M 27/00* (2006.01)

(Continued)

(52) U.S. Cl.

CPC ...... *A61F 13/00068* (2013.01); *A61F 2/2846* (2013.01); *A61F 13/00063* (2013.01);

(Continued)

(58) Field of Classification Search

CPC .. A61M 1/0088; A61M 27/00; A61M 1/0023; A61F 13/0068; A61F 2013/00536;

(Continued)

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

(Continued)

*Primary Examiner* — Susan Su
*Assistant Examiner* — Andrew J Mensh

(57) ABSTRACT

Provided is an apparatus that includes a scaffold with a gel or liquid composition deposed on at least a portion of a luminal surface, the gel or liquid composition adapted to include microbubbles. Also provided is a system that includes a source of reduced pressure, the above scaffold, a manifold adjacent the scaffold, and a conduit for providing fluid communication between the manifold and the source of reduced pressure. Additionally provided is a method that includes implanting the above scaffold at the tissue site and disrupting a substantial portion of the microbubbles to induce fluid flow to the scaffold. Further provided is an apparatus that includes a scaffold that comprises a slowly (Continued)

degradable material and a quickly degradable material. Additionally provided is a system for coupling nerve tissue and a microchip assembly.

10 Claims, 5 Drawing Sheets

Related U.S. Application Data

(60) Provisional application No. 61/234,692, filed on Aug. 18, 2009, provisional application No. 61/142,053, filed on Dec. 31, 2008, provisional application No. 61/142,065, filed on Dec. 31, 2008.

(51) Int. Cl.

| | |
|---|---|
| ***A61F 13/00*** | (2006.01) |
| ***A61K 38/18*** | (2006.01) |
| ***A61K 38/19*** | (2006.01) |
| ***A61K 38/22*** | (2006.01) |
| ***A61M 37/00*** | (2006.01) |
| ***A61N 5/06*** | (2006.01) |
| *A61M 31/00* | (2006.01) |
| *A61M 3/00* | (2006.01) |
| *A61F 13/20* | (2006.01) |
| *A61F 5/44* | (2006.01) |
| *A61F 2/28* | (2006.01) |
| *A61F 2/30* | (2006.01) |
| *A61B 17/88* | (2006.01) |
| *A61F 2/36* | (2006.01) |
| *A61K 49/22* | (2006.01) |

(52) U.S. Cl.

CPC .............. *A61K 38/18* (2013.01); *A61K 38/19* (2013.01); *A61K 38/22* (2013.01); *A61M 1/0088* (2013.01); *A61M 27/00* (2013.01); *A61M 37/00* (2013.01); *A61M 37/0092* (2013.01); *A61N 5/062* (2013.01); *A61B 17/88* (2013.01); *A61F 2002/2835* (2013.01); *A61F 2002/30784* (2013.01); *A61F 2002/368* (2013.01); *A61F 2013/00357* (2013.01); *A61F 2013/00927* (2013.01); *A61K 49/223* (2013.01); *A61M 1/0023* (2013.01)

(58) Field of Classification Search

CPC ................ A61F 13/00; A61F 13/00063; A61F 2002/30235; A61F 2002/368; A61F 2002/3694; A61F 2236/069; A61F 2013/0054; A61F 2/2846; A61F 2002/2835; A61F 2002/30784; A61K 49/223; A61B 17/88; A61B 2013/00927

USPC ......... 604/541, 543, 313, 315, 316, 286, 11, 604/305, 43, 355

See application file for complete search history.

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 3,902,497 | A | 9/1975 | Casey |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt et al. |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 5,919,434 | A | 7/1999 | Dugstad et al. |

(56) References Cited

U.S. PATENT DOCUMENTS

| | | | |
|---|---|---|---|
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,070,584 B2 | 7/2006 | Johnson et al. | |
| 7,169,151 B1 * | 1/2007 | Lytinas | A61B 17/88 606/86 R |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0225347 A1 * | 12/2003 | Argenta | A61B 17/88 601/6 |
| 2006/0079852 A1 | 4/2006 | Bubb et al. | |
| 2007/0100358 A2 | 5/2007 | Romero-Ortega et al. | |
| 2007/0219585 A1 * | 9/2007 | Cornet | A61B 17/88 606/221 |
| 2007/0225663 A1 | 9/2007 | Watt et al. | |
| 2010/0168771 A1 * | 7/2010 | Guldberg | A61L 27/3804 606/151 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Đ ukić, Ž. Maksimović, Đ . Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin

(56) References Cited

OTHER PUBLICATIONS (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

* cited by examiner

SYSTEMS FOR PROVIDING FLUID FLOW TO TISSUES

CROSS-REFERENCE TO RELATED APPLICATIONS

This application is a divisional of U.S. patent application Ser. No. 12/648,448, filed Dec. 29, 2009, entitled "Systems For Providing Fluid Flow To Issues", which claims the benefit of U.S. Provisional Application No. 61/234,692, filed Aug. 18, 2009, U.S. Provisional Application No. 61/142,053, filed Dec. 31, 2008, and U.S. Provisional Application No. 61/142,065, filed Dec. 31, 2008, all of which are hereby incorporated by reference.

BACKGROUND OF THE INVENTION

1. Field of the Invention

The present application relates generally to tissue engineering and in particular to systems and scaffolds suitable for use in treatment of tissue.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formation of granulation tissue. Typically, reduced pressure has been applied to tissue through a porous pad or other manifolding device. The porous pad contains pores that are capable of distributing reduced pressure to the tissue and channeling fluids that are drawn from the tissue. The porous pad often is incorporated into a dressing having other components that facilitate treatment. A scaffold can also be placed into a defect to support tissue growth into the defect. The scaffold is usually bioabsorbable, leaving new tissue in its place.

Scaffolds for reduced pressure treatment are described in, e.g., WO08/091521, WO07/092397, WO07/196590, WO07/106594. The adequacy of current scaffolds for reduced pressure treatment can be evaluated in light of current knowledge of wound healing. Injury to body tissues results in a wound healing response with sequential stages of healing that include hemostasis (seconds to hours), inflammation (hours to days), repair (days to weeks), and remodeling (weeks to months). A high level of homology exists across most tissue types with regards to the early phases of the wound healing process. However, the stages of healing for various tissues begin to diverge as time passes, with the involvement of different types of growth factors, cytokines, and cells. The later stages of the wound healing response are dependent upon the previous stages, with increasing complexity in the temporal patterning of and interrelationships between each component of the response.

Strategies to facilitate normal repair, regeneration, and restoration of function for damaged tissues have focused on methods to support and augment particular steps within this healing response, especially the latter aspects of it. To this end, growth factors, cytokines, extracellular matrix (ECM) analogs, exogenous cells, and various scaffolding technologies have been applied alone or in combination with one another. Although some level of success has been achieved using this approach, several key challenges remain. One main challenge is that the timing and coordinated influence of each cytokine and growth factor within the wound healing response complicate the ability to add individual exogenous factors at the proper time and in the correct coordination pattern. The introduction of exogenous cells also faces additional complications due to their potential immunogenicity as well as difficulties in maintaining cell viability.

Synthetic and biologic scaffolds have been utilized to provide three-dimensional frameworks for augmenting endogenous cell attachment, migration, and colonization. To date nearly all scaffolds have been designed with the idea that they can be made to work with in situ biology. Traditional scaffolding technologies, however, rely on the passive influx of endogenous proteins, cytokines, growth factors, and cells into the interstitium of the porous scaffold. As such, the colonization of endogenous cells into the scaffold is limited by the distance away from vascular elements, which provide nutrient support within a diffusion limit of the scaffold, regardless of tissue type. In addition, the scaffolds can also elicit an immunogenic or foreign body response that leads to an elongated repair process and formation of a fibrous capsule around the implant. Taken together, these complications can all lead to less than functional tissue regeneration at the injury site.

It would therefore be advantageous to provide additional systems to further direct healing and tissue growth. The present invention provides such systems.

BRIEF SUMMARY OF THE INVENTION

The scaffolds, systems and methods of the illustrative embodiments described herein provide active guidance of tissue regeneration through an implanted scaffold. In one embodiment, an apparatus for providing reduced pressure therapy and facilitating growth of tissue at a tissue site of a patient is provided that includes a scaffold adaptable for implantation at the tissue site, where the scaffold provides a structural matrix for the growth of the tissue and having a luminal surface, and a gel or liquid composition disposed on at least a portion of the luminal surface, the gel or liquid composition adapted to include microbubbles.

In another embodiment, a system for providing reduced pressure therapy and facilitating growth of tissue at a tissue site of a patient is provided that includes a source of reduced pressure for supplying reduced pressure, a scaffold adaptable for implantation at the tissue site, where the scaffold provides a structural matrix for the growth of the tissue and has a luminal surface, a gel or liquid composition deposed on at least a portion of the luminal surface, where the gel or liquid composition is adapted to include microbubbles, a manifold adjacent the scaffold, where the manifold distributes the reduced pressure to the scaffold, and a conduit for providing fluid communication between the manifold and the source of reduced pressure.

In a further embodiment, a method of providing reduced pressure therapy and facilitating growth of tissue at a tissue site of a patient is provided that includes implanting a scaffold at the tissue site, where the scaffold provides a structural matrix for the growth of the tissue and comprises a gel or liquid composition on a luminal surface, where the gel or liquid composition is adapted to include microbubbles, applying reduced pressure to the scaffold, and disrupting a substantial portion of the microbubbles to induce fluid flow to the scaffold.

In an additional embodiment, an apparatus for providing reduced pressure therapy and facilitating growth of tissue at a tissue site of a patient is provided that includes a scaffold adaptable for implantation at the tissue site, where the scaffold provides a structural matrix for the growth of the tissue and comprises a slowly degradable material, and a quickly degradable material, the quickly degradable material degrading faster than the slowly degradable material to form channels in the scaffold for the transfer of a fluid, and a manifold for providing reduced pressure to the scaffold, where the channels provide fluid communication between the manifold and the tissue site.

In a further embodiment, a system for coupling nerve tissue and a microchip assembly is provided that includes a source of reduced pressure, a biocompatible conduit adaptable for disposing adjacent nerve tissue, where the conduit is fluidly coupled to the source of reduced pressure, and a microchip assembly disposed in the conduit, where reduced pressure from the source of reduced pressure facilitates growth of the nerve tissue to operably connect to the microchip assembly.

Other objects, features, and advantages of the illustrative embodiments will become apparent with reference to the drawings and detailed description that follow.

DETAILED DESCRIPTION OF THE PREFERRED EMBODIMENT

Figure 1:
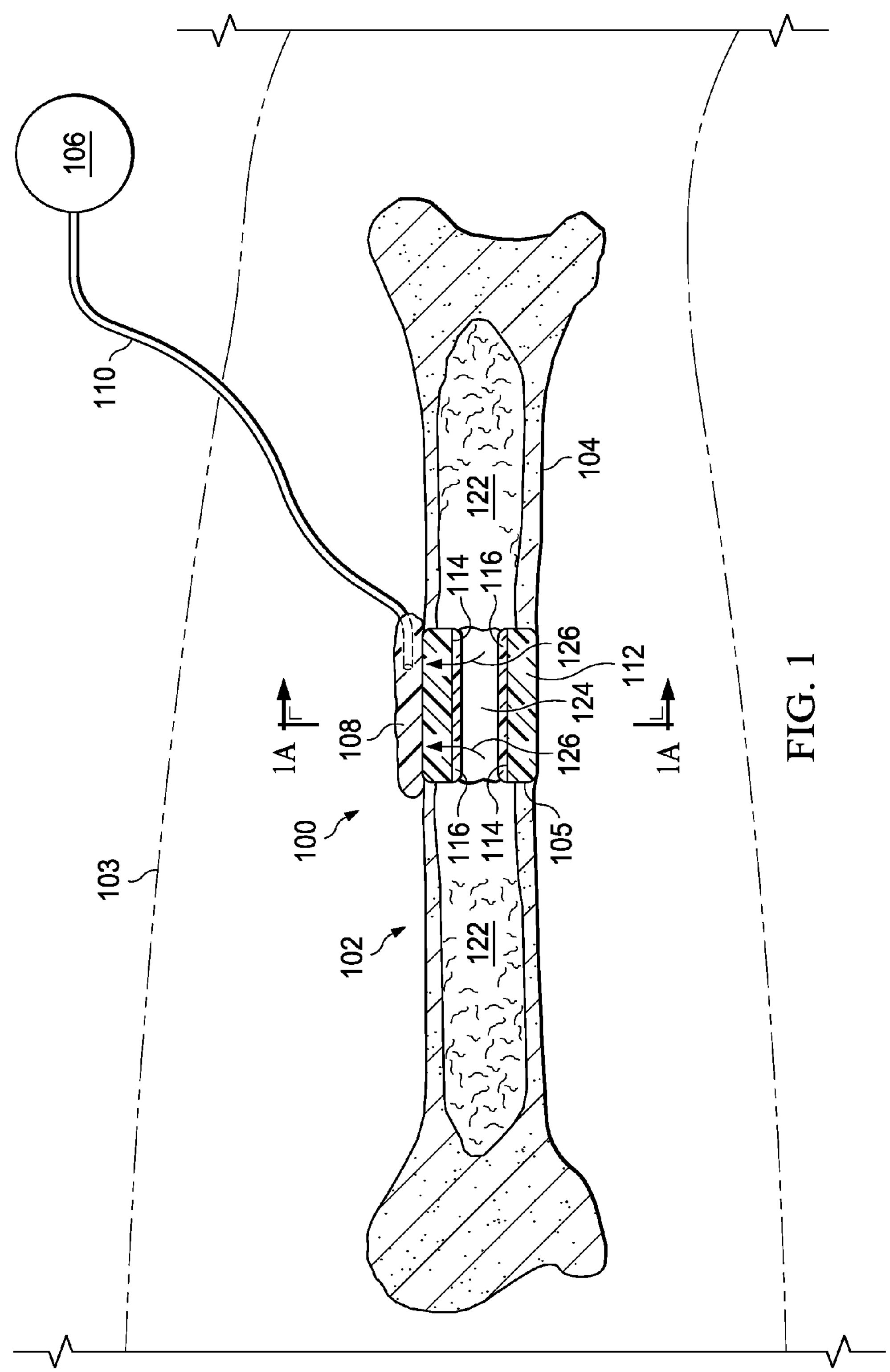
FIG. 1 is a system, shown in partial cross-section, for applying reduced pressure therapy to a tissue site of a patient.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Referring to FIGS. 1 and 2A-2C, a reduced pressure therapy system 100 for applying reduced pressure to a tissue site 102 of a patient 103 includes a reduced pressure source 106 that supplies reduced pressure, a manifold 108 fluidly coupled to the pressure source 106 via a conduit 110, and a scaffold 112 in fluid communication with the manifold 108. In this example, the tissue site 102 is a bone 104 having a wound 105 that is a gap in the diaphysis of the bone 104. The manifold 108 transfers the reduced pressure to the scaffold 112 that is implanted within the wound 105 of the bone 104.

The scaffold 112 may have a variety of shapes depending on the type of wound, and in this embodiment has a tubular shape to fill the gap or wound 105 within the bone 104. The tubular scaffold 112 has a single lumen or flow channel 124 extending axially through the scaffold 112 and having a luminal surface 114. The scaffold 112 may also have a substantially cylindrical shape having a plurality of lumens as necessary for growing new tissue within the wound 105. Ultimately, the scaffold 112 is colonized by cells and matrix proteins that flow primarily from the intramedullary space 122 of the bone 104 through the flow channel 124 in response to application of the negative pressure or other stimuli.

The luminal surface 114 of the scaffold 112 is coated with a chemical substance 116 having a solid, gelatinous, or liquid form that contains microbubbles 118 (not shown). The chemical substance 116 may include the microbubbles 118 that are pre-formed in the chemical substance 116 when applied to the luminal surface 114 of the flow channel 124. In other embodiments, the chemical substance 116 may comprise a composition that forms the microbubbles 118 after being applied to the luminal surface 114 of the flow channel 124 as a result of portions of the chemical substance 116 transitioning into a gaseous phase, i.e., a gaseous phase transition, in response to a stimulus or catalyst. After the scaffold 112 is implanted within the wound 105, the microbubbles 118 are disrupted as part of the therapy to induce fluid flow from the intramedullary space 122, through the flow channel 124 and into the scaffold 112 as identified by arrows 126.

Figure 2A:
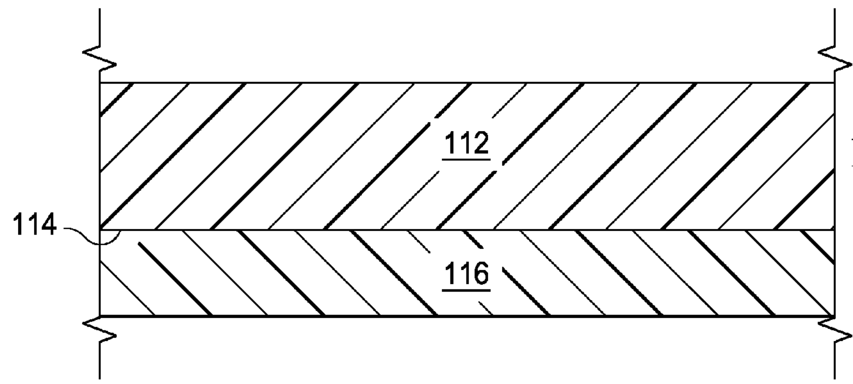
FIGS. 2A-2C shows the scaffold in the system of FIG. 1 at different points in time.
Figure 2B:
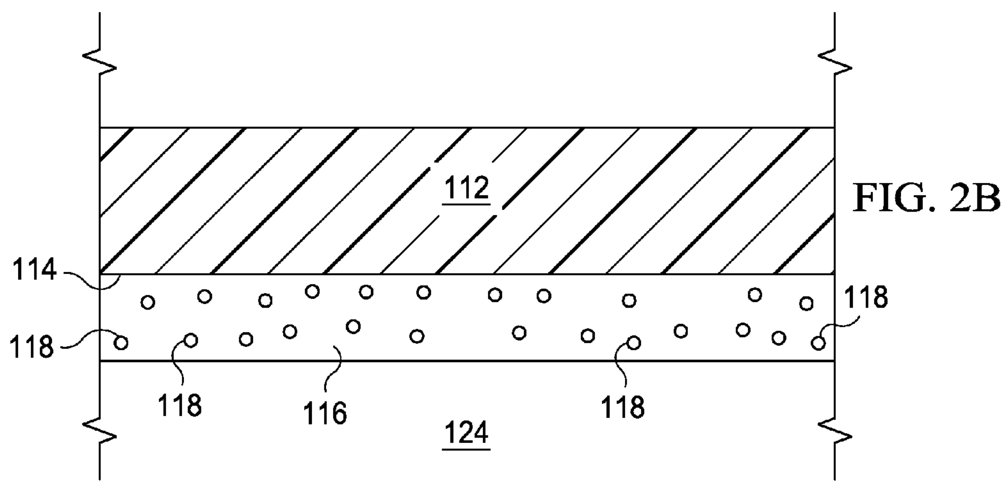
Figure 2C:
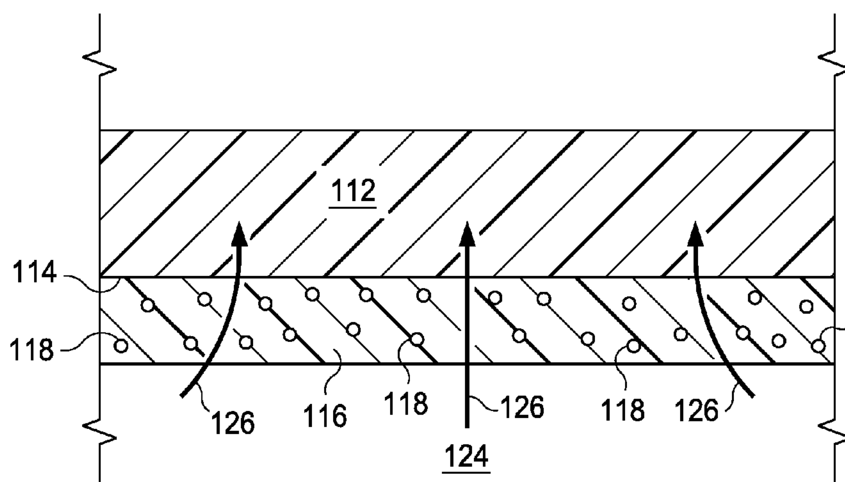

FIGS. 2A to 2C show the scaffold 112 and the chemical substance 116 at three different points in time. FIG. 2A shows the scaffold 112 and the chemical substance 116 disposed on the luminal surface 114 before the microbubbles 118 are formed and before the induction of a gaseous phase transition. FIG. 2B shows the chemical substance 116 containing the microbubbles 118 that were already formed when initially applied to the luminal surface 114, or were formed after application upon induction of a gaseous phase transition. The microbubbles 118 may be formed by a variety of stimuli such as, for example, by utilizing a chemical substance 116 that is responsive to high-frequency ultrasound and then exposing the chemical substance 116 to such ultrasound frequencies to create the microbubbles either before or after the chemical substance 116 is disposed on the luminal surface 114. Microbubbles 118 may also be formed by other stimuli including, for example, heat provided by an external source or the body itself, light energy, mechanical stimulation, or chemical stimulation.

When the microbubbles 118 are pre-formed in the chemical substance 116, implantation and the consequential heating of the scaffold 112 to body temperature may increase the size of pre-formed microbubbles 118 as described in WO 2006/12753. When the microbubbles 118 are not pre-formed, the gaseous phase transition of the chemical substance 116 may be induced by a temperature increase resulting from implanting the scaffold 112 into the wound 105 which is at a higher body temperature. In some embodiments, the chemical substance 116 has a composition that induces the gaseous phase transition at the body temperature of the mammal (e.g., 37° C. for humans). In other embodiments, the gaseous phase transition may be induced by sound waves or ultrasonic waves having a relatively low frequency within the range of about 20 kHz to about 500 kHz for example. The optimum wavelength for any particular chemical substance 116 can be determined by routine experimentation. Whatever method of induction is used, the gaseous phase transition can be induced either before or after implantation of the scaffold. The microbubbles 118 may be formed by a gaseous component of the chemical substance 116 such as, for example, perfluoropentane ($C_5F_{12}$) or decafluorobutane ($C_4F_{10}$). The microbubbles 118 are bubbles that are less than about 100 μm in diameter. In some embodiments, the microbubbles 118 are between about 1 μm in diameter and about 75 μm in diameter.

Any biocompatible gas may be used in the formation of the microbubbles 118, including nitrogen, oxygen, carbon dioxide, hydrogen, an inert gas (e.g., helium, argon, xenon or krypton), a sulfur fluoride (e.g., sulfur hexafluoride), an optionally halogenated silane such as methylsilane or dimethylsilane, a low molecular weight hydrocarbon such as an alkane, a cycloalkane, an alkene, an ether, a ketone, an ester, a halogenated low molecular weight hydrocarbon, or a mixture of any of the foregoing. In some embodiments, the gas used to form the microbubbles 118 comprises fluorine atoms, e.g., bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethylfluoride, sulfur hexafluoride, 1,1-difluoroethane and perfluorocarbons, e.g., perfluoropropane, perfluorobutanes and perfluoropentanes.

The microbubbles 118 may be formed by mixing a gas, or a compound that is a gas at body temperature, with an amphiphilic compound or a surfactant. See, e.g., PCT Patent Publication WO 2006/127853 and U.S. Patent Application Publication US 2005/0260189, both incorporated by reference. The surfactant in the chemical substance 116 used to form the microbubbles 118 may comprise a single compound or a combination of compounds. Examples of useful surfactants include lipids, including sterols, hydrocarbons, fatty acids and derivatives, amines, esters, sphingolipids, and thiol-lipids; block copolymers of polyoxypropylene; polyoxyethylene; sugar esters; fatty alcohols, aliphatic amine oxides; hyaluronic acid aliphatic esters and salts thereof, dodecyl poly-(ethyleneoxy)ethanol; nonylphenoxy poly(ethyleneoxy)ethanol; hydroxy ethyl starch; hydroxy ethyl starch fatty acid esters; dextrans; dextran fatty acid esters; sorbitol; sorbitol fatty acid esters; gelatin; serum albumins; phospholipid-containing surfactants (e.g., lecithins [phosphatidylcholines, dimyristoylphosphatidylcholine, dipalmitoylphosphatidylcholine or distearoylphosphatidylcholine, etc.], phosphatidic acids, phosphatidylethanolamines, phosphatidylserines, phosphatidylglycerols, phosphatidylinositols, cardiolipins, sphingomyelins); nonionic surfactants such as polyoxyethylene-polyoxypropylene copolymers, e.g., Pluronic surfactants; polyoxyethylene fatty acids including polyoxyethylene stearates, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oils, and the hydrogenated derivatives thereof; cholesterol; anionic surfactants. In some embodiments, the amphiphilic substance is a block copolymer, for example (poly(ethylene oxide)-block-poly(L-lactide)) (PEG-PLLA), poly(ethylene oxide)-block-poly(caprolactone)), or Pluronic P-105. In addition to the surfactant(s), other agents may be incorporated within the aqueous phase of the chemical substance 116. Such agents include conventional viscosity modifiers, buffers such as phosphate buffers or other conventional biocompatible buffers or pH adjusting agents such as acids or bases, osmotic agents (to provide isotonicity, hyperosmolarity, or hyposmolarity).

In some embodiments, the chemical substance 116 may further comprise a bioactive agent which may be contained within the microbubbles 118, where the bioactive agent is released when the microbubbles 118 are disrupted. The microbubbles 118 may encapsulate the bioactive agent which can be released depending on the therapy wherein the microbubbles 118 are disrupted as described below in more detail. The bioactive agent may also be present within the chemical substance 116 outside of the microbubbles 118, such as in solution or encapsulated in micelles of the surfactant, where the agent is slowly released (See, e.g., WO 2006/127853). In some embodiments, the bioactive agent is an antibiotic or a growth factor. Nonlimiting examples of useful bioactive growth factors for various applications are growth hormone (GH), a bone morphogenetic protein (BMP), transforming growth factor-α (TGF-α), a TGF-β, a fibroblast growth factor (FGF), granulocyte-colony stimulating factor (G-CSF), granulocyte/macrophage-colony stimulating factor (GM-CSF), epidermal growth factor (EGF), platelet derived growth factor (PDGF), insulin-like growth factor (IGF), vascular endothelial growth factor (VEGF), hepatocyte growth factor/scatter factor (HGF/SF), an interleukin, tumor necrosis factor-α (TNF-α) or nerve growth factor (NGF).

FIG. 2C shows the scaffold 112 and the chemical substance 116 after being subjected to a stimulus that disrupts the microbubbles 118 so that they rupture or collapse to facilitate fluid flow as represented by the arrows 126 through the flow channel 124 and the chemical substance 116 into the scaffold 112 as described above. The microbubbles 118 may be disrupted by a variety of stimuli such as, for example, by exposing the microbubbles 118 to high frequency ultrasound having a frequency in the range of about 1 MHz to about 5 MHz. Disruption of the microbubbles 118 creates openings in the chemical substance 116 that provide an increased area for fluids to occupy and that may also form passages for facilitating or enhancing fluid flow as described above including both gaseous fluid flow and liquid fluid flow such as fluid flow from the wound 105. In some embodiments, the direction of fluid flow can be controlled by concentrating the microbubbles 118 in different portions of the chemical substance 116 to direct flow toward a predetermined portion of the scaffold 112. In other embodiments, directional flow is enhanced by disrupting the microbubbles 118 sequentially across contiguous segments of the scaffold 112 to create directional changes in the fluid flow 126.

The term "scaffold" as used herein refers to a substance that provides a structural matrix for the growth of cells and/or the formation of tissue. A scaffold is often a three dimensional porous structure that may be infused with, coated with, or comprised of cells, growth factors, extracellular matrix components, nutrients, integrins, or other substances to promote cell growth. A scaffold can take on characteristics of a manifold by directing flow through the matrix. The scaffold 112 may have a variety of shapes including, for example, a substantially cylindrical shape such as a conduit fabricated for generating nerve fibers. An example of such a scaffold is described in U.S. Provisional Patent Applications 61/142,053 and 61/142,065. The scaffold 112 can be used in any tissue engineering application that could benefit from directed flow. Such scaffolds are useful for example, for encouraging long bone growth or for nerve regeneration, as discussed in U.S. Provisional Patent Application 61/142,053.

Nonlimiting examples of suitable scaffold 112 materials include extracellular matrix proteins such as fibrin, collagen, or fibronectin, and synthetic or naturally occurring polymers, including bioabsorbable or non-bioabsorbable polymers, such as polylactic acid (PLA), polyglycolic acid (PGA), polylactide-co-glycolide (PLGA), polyvinylpyrrolidone, polycaprolactone, polycarbonates, polyfumarates, caprolactones, polyamides, polysaccharides (including alginates [e.g., calcium alginate] and chitosan), hyaluronic acid, polyhydroxybutyrate, polyhydroxyvalerate, polydioxanone, polyorthoesthers, polyethylene glycols, poloxamers, polyphosphazenes, polyanhydrides, polyamino acids, polyortho esters, polyacetals, polycyanoacrylates, polyurethanes, polyacrylates, ethylene-vinyl acetate polymers and other acyl substituted cellulose acetates and derivatives thereof, polystyrenes, polyvinyl chloride, polyvinyl fluoride, polyvinylimidazole, chlorosulphonated polyolefins, polyethylene oxide, polyvinyl alcohol, Teflon®, hydrogels, gelatins, and nylon. The scaffold 112 can also comprise ceramics such as hydroxyapatite, coralline apatite, calcium phosphate, calcium sulfate, calcium carbonate or other carbonates, bioglass, allografts, autografts, xenografts, decellularized tissues, or composites of any of the above. In particular embodiments, the scaffold 112 comprises collagen, polylactic acid (PLA), polyglycolic acid (PGA), polylactide-co-glycolide (PLGA), a polyurethane, a polysaccharide, an hydroxyapatite, or a polytherylene glycol. Additionally, the scaffold 112 can comprise combinations of any two, three, or more materials, either in separate areas of the scaffold 112, or combined noncovalently, or covalently combined (e.g., copolymers such as a polyethylene oxide-polypropylene glycol block copolymers, or terpolymers), or combinations thereof. Suitable matrix materials are discussed in, for example, Ma and Elisseeff, 2005, and Saltzman, 2004.

Figure 3A:
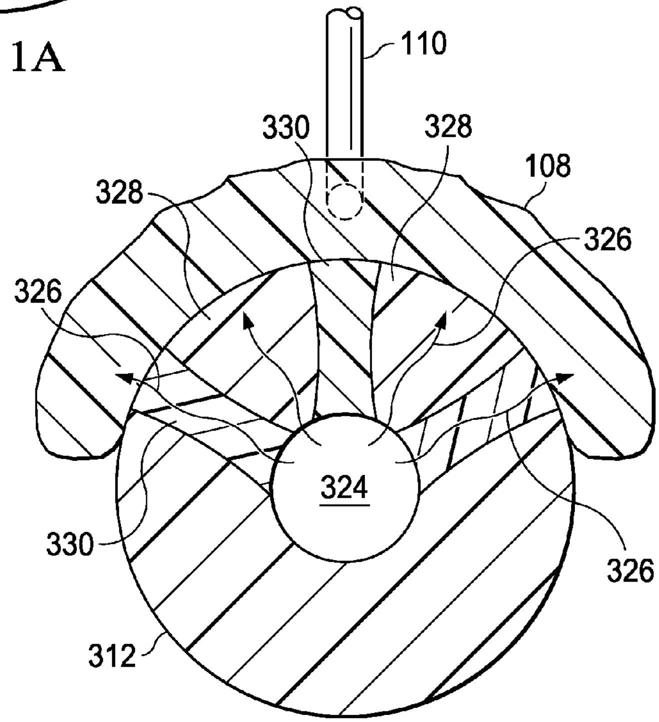
FIG. 3A is a cross-sectional view of the apparatus of FIG. 3 taken on the line 3A-3A.
Figure 3:
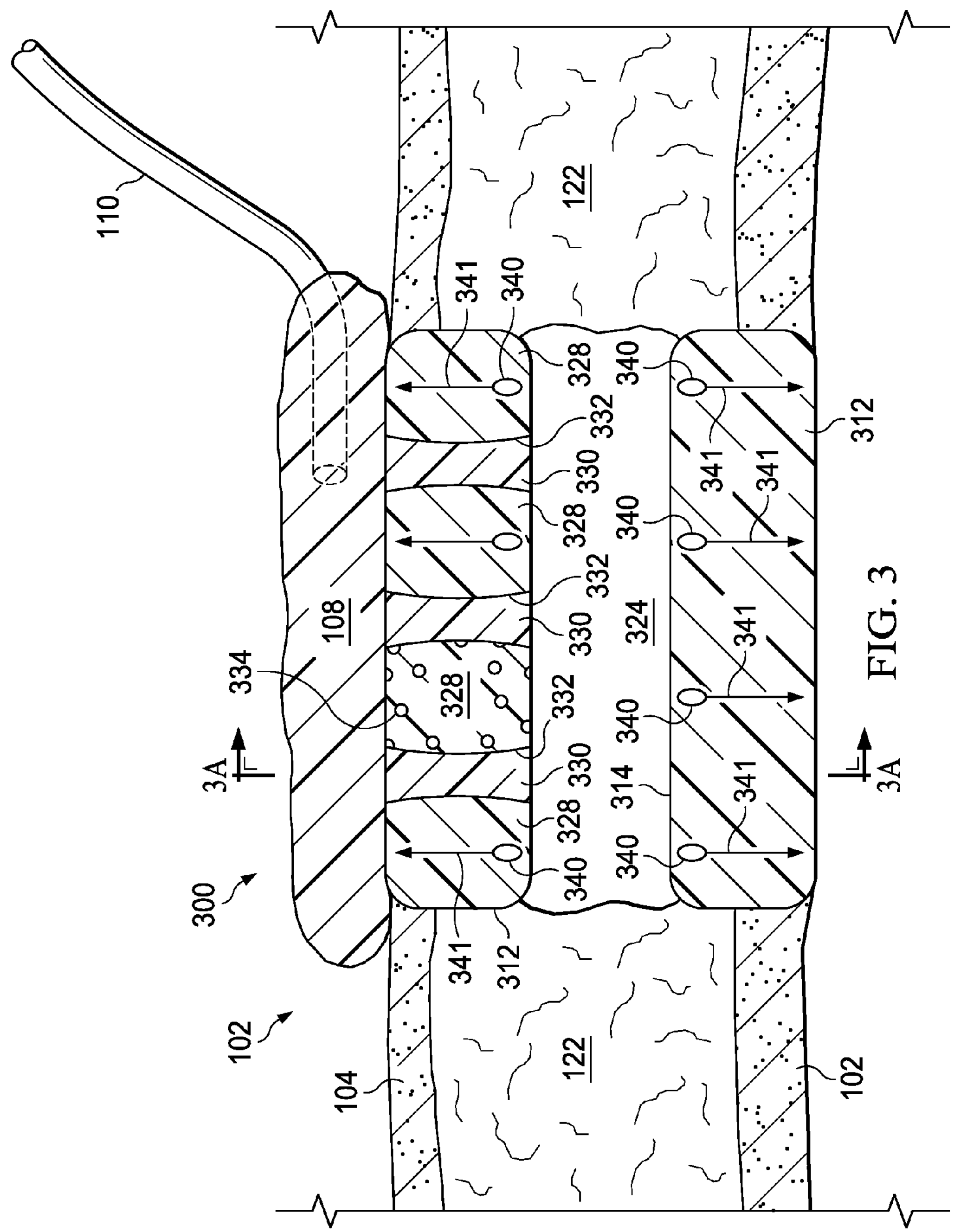
FIG. 3 is a cross-sectional view of a reduced pressure therapy apparatus in accordance with an illustrative embodiment.

Referring now to FIG. 3, another embodiment of a reduced pressure therapy system 300 having components similar to the reduced pressure therapy system 100 as shown by common numeric references. The reduced pressure system 300 comprises a scaffold 312 in fluid communication with the manifold 108 having all the characteristics of the scaffold 112 described above including, without limitation, a single lumen or flow channel 324 having a luminal surface 314. The luminal surface 314 may also be coated with a chemical substance 116 (not shown) containing microbubbles 118 as described above. The scaffold 312 may be formed from bioabsorbable materials that degrade at different rates to further enhance fluid flow through the scaffold 312. For example, the scaffold may be formed primarily from a first material or structural material 328 that may be degradable and a second material that degrades more quickly than the first material, i.e., degradable material such as, for example, a hydrocolloid that degrades in less than a day or two. The second material that degrades more quickly than the structural material 328 may be fabricated in the form of a channel 330 extending generally radially from the luminal surface 314 to the manifold 108. When the channel 330 of material degrades after the scaffold 312 is implanted within the wound 105, channel passages 332 are formed through the scaffold 312 to further facilitate the flow of fluids from the intramedullary space 122, through the flow channel 324, and into and through the scaffold 312.

The second material may also be formed in pockets 334 dispersed throughout the structural material 328 of the scaffold 312. The pockets 334 of degradable material may be used in addition to, or in lieu of, the channels 330 of degradable material and may degrade at a different rate when used in conjunction with the channels 330. When the pockets 334 of degradable material degrade after the scaffold 312 is implanted within the wound 105, pores (not shown) are formed in the structural material 328 that can absorb more fluids and/or provide passages to further facilitate fluid flow in addition to the channel passages 332 from the intramedullary space 122 to the manifold 108.

As indicated above, when the scaffold 312 is implanted in the wound and a reduced pressure is applied through the manifold 108, reduced pressure gradients flow through the scaffold 312 from the intramedullary space 122 of the bone 104 through the flow channel 324 and the channel passages 332 to facilitate the flow of fluids for delivering cells and beneficial proteins (e.g., growth factors and structural proteins) contained within the fluid into the scaffold 312. As the pockets 334 of degradable material dissolve, the pores in the structural material 328 of the scaffold 312 absorb the fluid from the intramedullary space 122 accelerating cell colonization of the scaffold 312. It should be understood that the pores in the structural material 328 and the channel passages 332 may be a permeable matrix of material after degradation having a permeability selected to control the rate at which the scaffold 312 absorbs such fluids. In other embodiments, the pores in the structural material 328 may be substantially void, and the channel passages 332 may also be substantially void or narrow, to further enhance the flow of fluid through the scaffold 312 and into the manifold 108.

Wound healing and tissue engineering can benefit from changing flow patterns as healing or tissue production/remodeling proceeds. Further, clogging of pores in the scaffold 312 and the channel passages 332 can cause flow through the scaffold 312 to decrease over time if no flow adjustments are made. Thus, therapy for treating the wound 105 can change over time. For example, based on the sequential stages of healing, i.e., hemostasis (seconds to hours), inflammation (hours to days), repair (days to weeks), and remodeling (weeks to months), a fresh wound (e.g., post surgery) would benefit from the provision of an agent that encourages hemostasis (e.g., platelet-activating factor, PAF) only if that agent were provided when healing first commenced, and would not be beneficial if only provided days after the wound was made. Conversely, an agent involved in repair or remodeling, e.g., TGF-β, would be optimally beneficial if provided after a day or two.

The structural material 328 of the scaffold 312 may be selected from a variety of degradable materials as long as they degrade more slowly than the channels 330 of degradable material. In one embodiment, the structural material 328 does not degrade completely for sixty days, while the channels 330 and/or pockets 334 of degradable material may degrade fully over a time period less than sixty days down to a day. The structural material 328 may be a biocompatible material that essentially does not degrade, such as metals or polyetheretherketone (PEEK). In some embodiments, the scaffold 312 is formed of structural material 328 that is already porous in addition to the channels 330 and/or pockets 334 of degradable material so that the porous structural material 328 accelerates fluid flow into and through the scaffold 312 and provides alternate passages for the fluid if the pores and channel passages 332 become clogged or blocked. The porous structural material 328 has pores averaging in size between about 50 and 500 microns. In other embodiments, the structural material 328 is not porous, and the degradation of the degradable material in the channels 330 and pockets 334 serve to commence flow through the scaffold 312. The scaffold 312 may be manufactured by a variety of processes as suitable for the selected material including, for example, those processes referred to above and further including salt leaching, freeze-drying, phase separation, weaving fibers, bonding non-woven fibers, or foaming.

In some embodiments, the degradable material of the channels 330 and pockets 334 comprise a hydrocolloid, such as those comprising a naturally occurring or chemically modified polysaccharide. Suitable chemically modified polysaccharides include carboxymethylcellulose gels, hydroxyethyl cellulose gels, hydroxy-propyl methyl cellulose gels, chitosan, low-methoxy pectins, cross-linked dextran and starch-acrylonitrile graft copolymer, starch sodium polyacrylate, and mixtures thereof. Suitable natural polysaccharides include alginic acid and its salts, pectins, galactomannans such as xanthan gum or guar gum locust bean gum, gum karaya, gum arable, hyaluronic acid and its salts, starches, and mixtures thereof. Suitable synthetic hydrocolloids include high molecular weight polyethylene glycols and polypropylene glycols, polymers of methyl vinyl ether and maleic acid and derivatives; polyvinyl pyrrolidone, polyethylene glycols, polypropylene glycols, metal and/or ammonium salts of polyacrylic acid and/or its copolymers, metal or ammonium salts of polystyrene sulfonic acid, and mixtures thereof.

The degradable material of the channels 330 and the pockets 334, as well as the structural material 328 to the extent degradable, may further comprise a bioactive agent, such as an antibiotic or a growth factor, including those discussed above. In some embodiments of the scaffold 312, the channels 330, and the pockets 334, as well as the structural material 328 to the extent degradable, may include more than one type of degradable material such as, for example, materials that degrade at two different rates to control the patterns of fluid flow for depositing cells or releasing bioactive agents in a predetermined pattern for the therapy being administered to the patient 103. For example, the channels 330 closest to the diaphysis of the bone 104 may be formed of material that degrades faster than the channels 330 in the center of the scaffold 312 to accelerate fluid flow at those locations, thereby accelerating the healing of the wound 105.

As indicated above, wound healing and tissue engineering can benefit from changing flow patterns as healing or tissue production/remodeling proceeds. Clogging of the pores in the scaffold 312 and the channel passages 332 can cause fluid flow through the scaffolding 312 to decrease over time if no flow adjustments are made. Consequently, the scaffold 312 may also include reduced pressure chambers 340 that when punctured or ruptured stimulate the flow of fluids and proteins along desired pathways 341 toward a central reduced pressure source such as the manifold 108. These low pressure chambers 340 can be of any shape such as, for example, spherical or elliptical, and contain a pressure that is lower than the ambient pressure within the scaffold 312. The pressure is sufficiently low within the low pressure chamber 340 so that the chambers 340 further induce fluid flow from the intramedullary space 122, through the flow channel 324, and into and through the scaffold 312 when the chambers 340 rupture and open. The low pressure chambers 340 are also useful for unclogging pores in the scaffold 312 and the channel passages 332 to facilitate fluid flow through the scaffold 312 as a flow adjustment during the therapy period for treating the wound 105.

The wound 105 may be an injury or defect, such as a fracture, located on or within any tissue site 102, including but not limited to, bone tissue, adipose tissue, muscle tissue, neural tissue, dermal tissue, vascular tissue, connective tissue, cartilage, tendons or ligaments. For example, the wound 105 can include burns, incisional wounds, excisional wounds, ulcers, traumatic wounds, and chronic open wounds. The wound 105 may also be any tissue that is not necessarily injured or defected, but instead is an area in which it is desired to add or promote growth of additional tissue, such as bone tissue. For example, reduced pressure tissue treatment may be used in certain tissue areas to grow additional tissue that may be harvested and transplanted to another tissue location. The tissue site 102 may also include sites for in vitro and in vivo maintenance of endogenous or exogenous grafts, and supportive scaffolds for subsequent implantation into the patient 103. The patient 103 may be any mammal, such as a mouse, rat, rabbit, cat, dog, or primate, including humans.

In the context of this specification, the term "reduced pressure" generally refers to a pressure that is less than the ambient pressure at a tissue site that is subjected to treatment. In most cases, this reduced pressure will be less than the atmospheric pressure where the patient is located. Although the terms "vacuum" and "negative pressure" may be used to describe the pressure applied to the tissue site, the actual pressure applied to the tissue site may be significantly greater than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure. Reduced pressure treatment typically applies reduced pressure at −5 mm Hg to −500 mm Hg, more usually −5 to −300 mm Hg, including but not limited to −50, −125, or −175 mm Hg.

The term "manifold" as used herein generally refers to a substance or structure that is provided to assist in applying reduced pressure to, delivering fluids to, or removing fluids from the tissue site 102. The manifold 108 typically includes a plurality of flow channels or pathways that distribute fluids provided to and removed from the tissue site 102 around the manifold 108. In one illustrative embodiment, the flow channels or pathways are interconnected to improve distribution of fluids provided or removed from the tissue site 102. The manifold 108 may be a biocompatible material that is capable of being placed in contact with the tissue site 102 and distributing reduced pressure to the tissue site 102. Examples of manifolds 108 may include, for example, without limitation, devices that have structural elements arranged to form flow channels, such as, for example, cellular foams, open-cell foams, porous tissue collections, liquids, gels, and foams that include, or cure to include, flow channels. The manifold 108 may be porous and may be made from foam, gauze, felted mat, or any other material suited to a particular biological application. In one embodiment, the manifold 108 is a porous foam and includes a plurality of interconnected cells or pores that act as flow channels. The porous foam may be a polyurethane, open-cell, reticulated foam such as GranuFoam®, manufactured by Kinetic Concepts, Inc. of San Antonio, Tex. Other embodiments might include "closed cells." These closed-cell portions of the manifold may contain a plurality of cells, the majority of which are not fluidly connected to adjacent cells. The closed cells may be selectively disposed in the manifold 108 to prevent transmission of fluids through perimeter surfaces of the manifold 108. In some situations, the manifold 108 may also be used to distribute fluids such as medications, antibacterials, growth factors, and various solutions to the wound 105. Other layers may be included in or on the manifold 108, such as absorptive materials, wicking materials, hydrogels, hydrophobic materials, and hydrophilic materials.

As described above, the reduced pressure therapy system 100 applies reduced pressure to the wound 105 which may be distributed uniformly through the scaffold 112. In some embodiments, the scaffold distributes reduced pressure discontinuously through the scaffolds 112 and 312 rather than being distributed in some uniform fashion thereby creating a reduced pressure gradient. For example, the reduced pressure is not delivered uniformly via a single point source, or via a plurality of inlets along a linear flow passage, or through a substantially homogeneous distribution manifold. In some embodiments, the reduced pressure gradient is discontinuous spatially, discontinuous in magnitude, or discontinuous over time. Consequently, the reduced pressure gradients may occur throughout the wound 105.

Figure 1A:
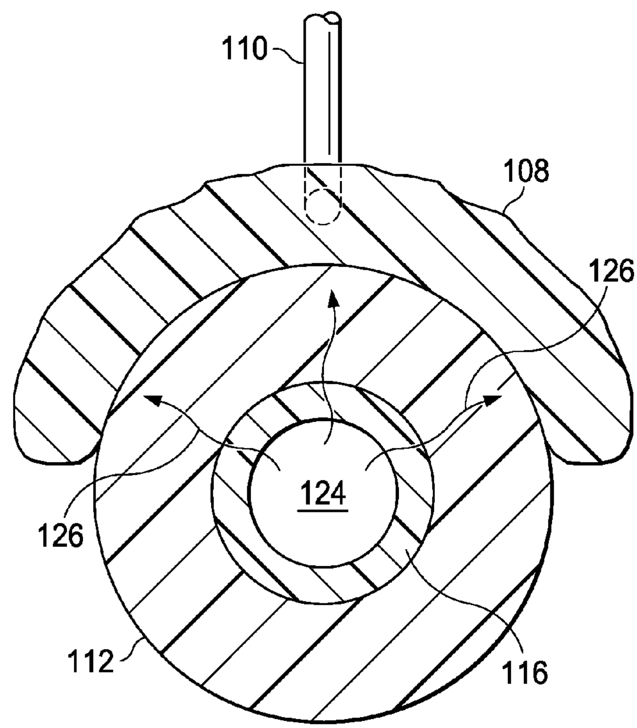
FIG. 1A is a cross-section view of the system of FIG. 1 taken on the line 1A-1A.

A gradient is the rate of change of any variable physical quantity in addition to reduced pressure including, without limitation, biologic gradients, thermal gradients, electrical gradients, magnetic gradients, chemical gradients, or positive pressure gradients. The manifold 108 and the scaffolds 112 and 312 may be designed to distribute gradients for these other physical characteristics. Referring to FIGS. 1A and 3A, for example, the manifold 108 and the scaffolds 112 and 312 may distribute reduced pressure gradients and/or biologic gradients as indicated by the arrows 126 and 326, respectively, as described above in more detail and as further described in U.S. Provisional Patent Applications 61/142,053 and 61/142,065, which are hereby incorporated by reference. The circumferential scaffolds 112 and 312 draw fluid radially from the intramedullary space 122 of the bone 104 (not shown) through their respective flow channels 124 and 324 in response to the reduced pressure or other stimuli, but in a discontinuous fashion to create gradients to further promote tissue growth and/or tissue healing. Thus, the methods and systems of the present invention provide a means for active guidance of tissue regeneration through the implanted scaffolds 112 and 312 or within a compromised site, such as wound 105, to promote functional recovery utilizing these physical gradients. As such, these methods and systems provide an active mechanism by which to promote the endogenous deposition of proteins and organization of the provisional matrix with biochemical and physical cues to direct cellular colonization of the scaffolds 112 and 312 or tissue space within the wound 105.

Figure 4:
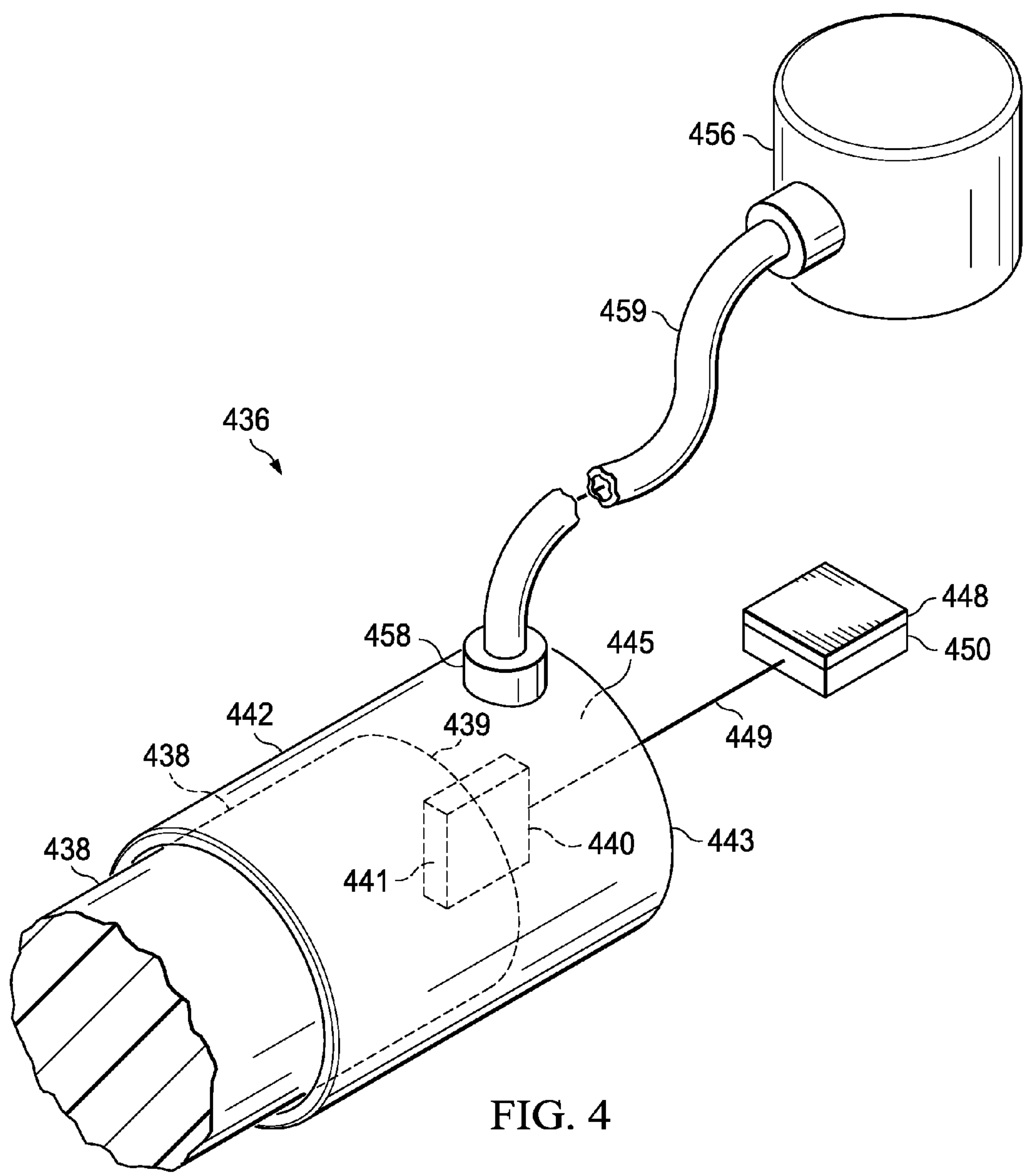
FIG. 4 is an illustrative embodiment of a system for connecting nerve tissue with a microchip assembly.

Referring to FIG. 4, an illustrative embodiment of a system 436 for coupling nerve tissue 438 to a microchip assembly 440 is shown. The nerve tissue 438 of this embodiment may have been damaged as a result of trauma so that only one severed end 439 remains. As used herein, the term “coupled” includes indirect coupling via a separate object and includes direct coupling. The term “coupled” also encompasses two or more components that are continuous with one another by virtue of each of the components being formed from the same piece of material. Also, the term “coupled” may include chemical, mechanical, thermal, or electrical coupling. Fluid coupling means that fluid is in communication between the designated parts or locations.

The microchip assembly 440 and the severed end 439 of the nerve tissue 438 are positioned within a biocompatible nerve conduit 442 that is generally tubular in shape for receiving and sealing the nerve tissue 438 at one end and closed by a conduit end wall 443 at the other end to form a luminal space 445 between the severed end 439 of the nerve tissue 438 and the conduit end wall 443. The microchip assembly 440 has a contact surface 441 positioned adjacent the severed end 439 and is electrically coupled to an electronic control unit 448 via a connection 449 that runs through the conduit end wall 443. The connection 449 that electrically couples the electronic control unit 448 to the microchip assembly 440 may be, for example, a hard-wire connection or a wireless connection. The electronic control unit 448 may also include a battery 450 for providing power to the microchip assembly 440 via the connection 449. It should be understood that both the electronic control unit 448 and the battery 450 may be integrated with the microchip assembly 440 within the luminal space 445 inside the nerve conduit 442.

The nerve conduit 442 is fluidly coupled to a reduced pressure source 456 via a conduit 459 and a manifold 458 that distributes reduced pressure from the reduced pressure source 456 to the luminal space 445. The reduced pressure in the luminal space 445 provides a flow pattern to the severed end 439 of the nerve tissue 438 and its interface with the contact surface 441 of the microchip assembly 440 to promote growth and/or regeneration of the nerve tissue 438. More specifically, the reduced pressure causes the fibers in the nerve tissue 438 to grow and operatively connect to the contact surface 441 of the microchip assembly 440. The manifold 458 may be bioresorbable to facilitate removal of the conduit 459 after the nerve tissue 438 has operatively connected to the contact surface 441 of the microchip assembly 440. The nerve conduit 442 itself may also be bioresorbable after sufficient healing of the nerve tissue 438 so that it does not need to be removed to avoid disrupting the operative connection between the severed end 439 of the nerve tissue 438 and the contact surface 441 of the microchip assembly 440.

The electronic control unit 448 controls a prosthetic or orthotic device (not shown) such as an artificial hand. To control the prosthetic or orthotic device, the electronic control unit 448 may include a radio frequency (RF) transceiver for sending radio signals to the prosthetic or orthotic device. In other embodiments, the electronic control unit 448 may be contained within the prosthetic or orthotic device for directly controlling movement. The connection between the severed end 439 of nerve tissue 438 and the contact surface 441 of the microchip assembly 440 allows a patient to control movement of such devices using thought-controlled nerve firing as an input for the regenerated nerve tissue 438 via the microchip assembly 440. The system 436 may be used as an interface device to restore motor control after nerve trauma, or to establish nerve-directed motor control of an orthotic or prosthetic device.

REFERENCES

Anderson E J et al., Tissue Eng. 13:2525-38 (2007).

Anderson E J and Tate M L K, Tissue Eng. 13:2525-2538 (2007).

Brody S and Pandit A, J Biomed Mater Res B Appl Biomater. 83:16-43 (2007).

Gemmiti C V and Guldberg R E, Tissue Eng. 12:469-79 (2006).

Lago N et al., IEEE Trans. Biomed. Eng. 54:1129-37 (2007).

Ma P X and Elisseeff J, ed. Scaffolding in Tissue Engineering, CRC, ISBN 1574445219 (2005).

Manwaring M E et al., Biomaterials 22:3155-3168 (2001).

Manwaring M E et al., Biomaterials 25:3631-3638 (2004).

Mercier et al., Biomaterials 26:1945-1952 (2005).

Mikos A G et al., J. Biomed. Mater. Res 27:183-189 (2004).

Norman J J and Desai T A, Ann Biomed Eng 34:89-101 (2006).

Pfister B J et al., Neurosurgery 60:137-41 (2007).

Saltzman W M, Tissue Engineering: Engineering Principles for the Design of Replacement Organs and Tissues, Oxford ISBN 019514130X (2004).

Sachlos E and Czernuzka J T, Eur. Cells and Mat 5:29-40 (2003).

Segvich S et al., J. Biomed Mater Res B: Appl. Biomater 84B:340-349 (2008).

Shimko D A et al., J Biomed Mater Res B: Appl Biomater 73:315-24 (2005).

Takahashi K and Yamanaka S, Cell 126: 663-76 (2006).

Tan S D et al., Bone 41:745-751 (2007).

Tan S D et al., Biochem Biophys Res Comm 369: 1150-1154 (2008)/Walsh

Walsh J F et al., Tissue Eng. 11:1085-1094 (2005).

Wen X et al., pp. 1-23 in Handbook of Nanostructured Biomaterials and Their Applications in Nanobioechnology, H. S. Nalwa, ed. ISBN 1-58883-033-0 (2005).

PCT Patent Publication WO06/004951.

PCT Patent Publication WO06/127853.

PCT Patent Publication WO07/092397.

PCT Patent Publication WO07/106594.

PCT Patent Publication WO07/196590.

PCT Patent Publication WO08/091521.

U.S. Patent Publication US 2003/0225347.

U.S. Patent Publication US 2005/0260189.

U.S. Patent Publication US 2008/0033324.

U.S. Patent Publication US 2008/0208358.

U.S. Pat. No. 4,787,906.

U.S. Pat. No. 6,103,255.

U.S. Pat. No. 6,365,146.

U.S. Pat. No. 6,696,575.

U.S. Pat. No. 7,160,553.

U.S. Pat. No. 7,384,786.

U.S. Provisional Patent Application 61/142,053.

U.S. Provisional Patent Application 61/142,065.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

In view of the above, it will be seen that the advantages of the invention are achieved and other advantages attained. As various changes could be made in the above methods and compositions without departing from the scope of the invention, it is intended that all matter contained in the above description and shown in the accompanying drawings shall be interpreted as illustrative and not in a limiting sense.

We claim:

1. A method for providing reduced pressure to a tissue site to facilitate tissue growth, the tissue site comprising a gap in the diaphysis of a bone, the method comprising:

providing a scaffold, the scaffold being tubular in shape and having a luminal surface forming at least one channel, the at least one channel at least partially covered by a chemical substance containing microbubbles;

implanting the scaffold in the tissue site so that the at least one channel is in direct fluid communication with an intramedullary space of the tissue site;

providing reduced pressure to the tissue site through the scaffold; and disrupting a substantial portion of the microbubbles to induce the flow of fluids within the scaffold.

2. The method of claim 1, wherein the chemical substance forms microbubbles in response to a stimulus that induces a gaseous phase transition in the chemical substance.

3. The method of claim 1, wherein the microbubbles are pre-formed in the chemical substance.

4. The method of claim 1, further comprising:

inducing a gaseous phase transition in the chemical substance to form the microbubbles after implanting the scaffold.

5. The method of claim 4, wherein inducing the gaseous phase transition in the chemical substance includes exposing the chemical substance to the body temperature of the patient.

6. The method of claim 1, wherein disrupting the substantial portion of the microbubbles includes inducing gradients in the reduced pressure.

7. The method of claim 1, wherein disrupting the substantial portion of the microbubbles includes inducing directional changes in the reduced pressure by sequentially disrupting the microbubbles across contiguous segments of the scaffold.

8. The method of claim 1, wherein disrupting the substantial portion of the microbubbles includes exposing the chemical substance to ultrasound energy.

9. The method of claim 1, wherein disrupting the substantial portion of the microbubbles includes exposing the chemical substance to light energy.

10. The method of claim 1, wherein the scaffold includes pre-formed low-pressure chambers and the method further comprises rupturing the pre-formed low-pressure chambers.

* * * * *